(12) United States Patent
Roorda et al.

(10) Patent No.: US 7,247,313 B2
(45) Date of Patent: *Jul. 24, 2007

(54) POLYACRYLATES COATINGS FOR IMPLANTABLE MEDICAL DEVICES

(75) Inventors: Wouter E. Roorda, Palo Alto, CA (US); Ni Ding, San Jose, CA (US); Stephen D. Pacetti, San Jose, CA (US); Eugene T. Michal, San Francisco, CA (US); Ashok A. Shah, San Jose, CA (US); Syed F. A. Hossainy, Fremont, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 177 days.

This patent is subject to a terminal disclaimer.

(21) Appl. No.: 10/176,504

(22) Filed: Jun. 21, 2002

(65) Prior Publication Data

US 2005/0106203 A1 May 19, 2005

Related U.S. Application Data

(63) Continuation-in-part of application No. 09/894,293, filed on Jun. 27, 2001, now abandoned.

(51) Int. Cl.
*A61F 2/02* (2006.01)
*A61K 9/00* (2006.01)

(52) U.S. Cl. .................. 424/423; 424/426; 424/400
(58) Field of Classification Search ................ 424/423, 424/422, 400, 426; 623/1.16, 1.42
See application file for complete search history.

(56) References Cited

U.S. PATENT DOCUMENTS

| | | | |
|---|---|---|---|
| 2,968,649 A | 1/1961 | Pailthorp et al. | |
| 3,051,677 A | 8/1962 | Rexford | |
| 3,178,399 A | 4/1965 | Lo | |
| 3,324,069 A | 6/1967 | Koblitz et al. | |
| 3,779,805 A | 12/1973 | Alsberg | |
| 3,856,827 A | 12/1974 | Cavitt | |
| 4,076,929 A | 2/1978 | Dohany | |
| 4,197,380 A | 4/1980 | Chao et al. | |

(Continued)

FOREIGN PATENT DOCUMENTS

DE 19723723 A1 12/1998

(Continued)

OTHER PUBLICATIONS

Rolling Therapeutic Agent Loading Device for Therapeutic Agent Delivery or Coated Stent, Research Disclosure, Kenneth Mason Publications, Hampshire, GB, No. 434, p. 975 (Jun. 2000).

(Continued)

*Primary Examiner*—Michael G. Hartley
*Assistant Examiner*—Blessing Fubara
(74) *Attorney, Agent, or Firm*—Squire, Sanders & Dempsey L.L.P.

(57) ABSTRACT

A coating for a medical device, particularly for a drug eluting stent, is described. The coating can include a polyacrylate, a blend of polyacrylates, or a blend of the polyacrylate with other polymers, for example, poly(ethylene-co-vinyl alcohol).

21 Claims, 2 Drawing Sheets

U.S. PATENT DOCUMENTS

| | | |
|---|---|---|
| 4,304,010 A | 12/1981 | Mano |
| 4,346,710 A | 8/1982 | Thanawalla et al. |
| 4,353,960 A | 10/1982 | Endo et al. |
| 4,399,264 A | 8/1983 | Squire |
| 4,413,359 A | 11/1983 | Akiyama et al. |
| 4,423,183 A | 12/1983 | Close |
| 4,485,250 A | 11/1984 | Squire |
| 4,530,569 A | 7/1985 | Squire |
| 4,564,013 A | 1/1986 | Lilenfeld et al. |
| 4,569,978 A | 2/1986 | Barber |
| 4,632,842 A | 12/1986 | Karwoski et al. |
| 4,636,346 A | 1/1987 | Gold et al. |
| 4,718,907 A | 1/1988 | Karwoski et al. |
| 4,733,665 A | 3/1988 | Palmaz |
| 4,749,585 A | 6/1988 | Greco et al. |
| 4,754,009 A | 6/1988 | Squire |
| 4,770,939 A | 9/1988 | Sietsess et al. |
| 4,800,882 A | 1/1989 | Gianturco |
| 4,871,357 A | 10/1989 | Hsu et al. |
| 4,876,109 A | 10/1989 | Mayer et al. |
| 4,886,062 A | 12/1989 | Wiktor |
| 4,897,457 A | 1/1990 | Nakamura et al. |
| 4,908,404 A | 3/1990 | Benedict et al. |
| 4,910,276 A | 3/1990 | Nakamura et al. |
| 4,931,287 A | 6/1990 | Bae et al. .................. 424/484 |
| 4,935,477 A | 6/1990 | Squire |
| 4,948,851 A | 8/1990 | Squire |
| 4,973,142 A | 11/1990 | Squire |
| 4,975,505 A | 12/1990 | Squire |
| 4,977,008 A | 12/1990 | Squire |
| 4,977,025 A | 12/1990 | Squire |
| 4,977,026 A | 12/1990 | Squire |
| 4,977,297 A | 12/1990 | Squire |
| 4,977,901 A | 12/1990 | Ofstead .................... 128/772 |
| 4,982,056 A | 1/1991 | Squire |
| 4,985,308 A | 1/1991 | Squire |
| 4,999,248 A | 3/1991 | Squire |
| 5,000,547 A | 3/1991 | Squire |
| 5,006,382 A | 4/1991 | Squire |
| 5,030,394 A | 7/1991 | Sietses et al. |
| 5,047,020 A | 9/1991 | Hsu |
| 5,051,114 A | 9/1991 | Nemser et al. |
| 5,051,978 A | 9/1991 | Mayer et al. |
| 5,053,048 A | 10/1991 | Pinchuk |
| 5,076,659 A | 12/1991 | Bekiarian et al. |
| 5,093,427 A | 3/1992 | Barber |
| 5,107,852 A | 4/1992 | Davidson et al. |
| 5,110,645 A | 5/1992 | Matsumoto et al. |
| 5,112,457 A | 5/1992 | Marchant .................... 204/165 |
| 5,176,972 A | 1/1993 | Bloom et al. |
| 5,185,408 A | 2/1993 | Tang et al. |
| 5,246,451 A | 9/1993 | Trescony et al. |
| 5,276,121 A | 1/1994 | Resnick |
| 5,296,283 A | 3/1994 | Froggatt |
| 5,302,385 A | 4/1994 | Khan et al. |
| 5,308,685 A | 5/1994 | Froggatt |
| 5,310,838 A | 5/1994 | Hung et al. |
| 5,324,889 A | 6/1994 | Resnick |
| 5,326,839 A | 7/1994 | Resnick |
| 5,328,471 A | 7/1994 | Slepian ...................... 604/101 |
| 5,336,518 A | 8/1994 | Narayanan et al. |
| 5,338,608 A | 8/1994 | Resnick |
| 5,342,348 A | 8/1994 | Kaplan |
| 5,353,368 A | 10/1994 | Resnick |
| 5,354,910 A | 10/1994 | Hung et al. |
| 5,368,566 A | 11/1994 | Crocker |
| 5,380,299 A | 1/1995 | Fearnot et al. |
| 5,383,853 A | 1/1995 | Jung et al. |
| 5,383,928 A | 1/1995 | Scott et al. |
| 5,395,311 A | 3/1995 | Andrews |
| 5,403,341 A | 4/1995 | Solar |
| 5,408,020 A | 4/1995 | Hung et al. |
| 5,417,969 A | 5/1995 | Hsu et al. |
| 5,443,458 A | 8/1995 | Eury |
| 5,447,724 A | 9/1995 | Helmus et al. |
| 5,455,040 A | 10/1995 | Marchant ..................... 424/426 |
| 5,464,650 A | 11/1995 | Berg et al. .................... 427/2.3 |
| 5,545,208 A | 8/1996 | Wolff et al. |
| 5,560,463 A | 10/1996 | Link et al. |
| 5,562,734 A | 10/1996 | King |
| 5,569,463 A | 10/1996 | Helmus et al. |
| 5,575,818 A | 11/1996 | Pinchuk |
| 5,578,073 A | 11/1996 | Haimovich et al. ............ 623/1 |
| 5,584,877 A | 12/1996 | Miyake et al. ................. 623/1 |
| 5,591,224 A | 1/1997 | Schwartz et al. |
| 5,604,283 A | 2/1997 | Wada et al. |
| 5,605,696 A | 2/1997 | Eury et al. .................... 424/423 |
| 5,616,608 A | 4/1997 | Kinsella et al. |
| 5,628,728 A | 5/1997 | Tachibana et al. |
| 5,632,771 A | 5/1997 | Boatman et al. |
| 5,632,776 A | 5/1997 | Kurumatani et al. |
| 5,632,840 A | 5/1997 | Campbell |
| 5,635,201 A | 6/1997 | Fabo |
| 5,667,767 A | 9/1997 | Greff et al. ............... 424/9.411 |
| 5,670,558 A | 9/1997 | Onishi et al. ................ 523/112 |
| 5,679,400 A | 10/1997 | Tuch |
| 5,684,061 A | 11/1997 | Ohnishi et al. |
| 5,691,311 A | 11/1997 | Maraganore et al. |
| 5,697,967 A | 12/1997 | Dinh et al. |
| 5,700,286 A | 12/1997 | Tartaglia et al. ................ 623/1 |
| 5,713,949 A | 2/1998 | Jayaraman |
| 5,716,981 A | 2/1998 | Hunter et al. ............... 514/449 |
| 5,750,234 A | 5/1998 | Johnson et al. |
| 5,758,205 A | 5/1998 | Hara et al. |
| 5,759,205 A | 6/1998 | Valentini ..................... 623/16 |
| 5,760,118 A | 6/1998 | Sinclair et al. |
| 5,776,184 A | 7/1998 | Tuch |
| 5,804,318 A | 9/1998 | Pinchuk et al. |
| 5,820,917 A | 10/1998 | Tuch |
| 5,824,048 A | 10/1998 | Tuch |
| 5,824,049 A | 10/1998 | Ragheb et al. .................. 623/1 |
| 5,827,587 A | 10/1998 | Fukushi |
| 5,830,178 A | 11/1998 | Jones et al. .................... 604/49 |
| 5,837,008 A | 11/1998 | Berg et al. |
| 5,837,313 A | 11/1998 | Ding et al. ................. 427/2.21 |
| 5,851,508 A | 12/1998 | Greff et al. ............... 424/9.411 |
| 5,858,746 A | 1/1999 | Hubbell et al. .............. 435/177 |
| 5,858,990 A | 1/1999 | Walsh ......................... 514/44 |
| 5,860,963 A | 1/1999 | Azam et al. |
| 5,861,168 A | 1/1999 | Cooke et al. |
| 5,865,814 A | 2/1999 | Tuch .......................... 604/265 |
| 5,869,127 A | 2/1999 | Zhong |
| 5,873,904 A | 2/1999 | Ragheb et al. .................. 623/1 |
| 5,874,165 A | 2/1999 | Drumheller |
| 5,879,697 A | 3/1999 | Ding et al. |
| 5,897,911 A | 4/1999 | Loeffer |
| 5,900,425 A | 5/1999 | Kanikanti et al. |
| 5,911,704 A | 6/1999 | Humes |
| 5,921,933 A | 7/1999 | Sarkis et al. |
| 5,922,393 A | 7/1999 | Jayaraman |
| 5,928,279 A | 7/1999 | Shannon et al. |
| 5,932,299 A | 8/1999 | Katoot |
| 5,945,115 A | 8/1999 | Dunn et al. |
| 5,971,954 A | 10/1999 | Conway et al. ................ 604/96 |
| 5,980,928 A | 11/1999 | Terry ......................... 424/427 |
| 5,980,972 A | 11/1999 | Ding ......................... 427/2.24 |
| 5,997,517 A | 12/1999 | Whitbourne ................ 604/265 |
| 6,015,541 A | 1/2000 | Greff et al. ................. 424/1.25 |
| 6,033,724 A | 3/2000 | Molitor |
| 6,042,875 A | 3/2000 | Ding et al. ................. 427/2.24 |
| 6,051,648 A | 4/2000 | Rhee et al. ................. 525/54.1 |
| 6,056,993 A | 5/2000 | Leidner et al. ............. 427/2.25 |
| 6,060,451 A | 5/2000 | DiMaio et al. ................ 514/13 |
| 6,060,534 A | 5/2000 | Ronan et al. |

| | | | | |
|---|---|---|---|---|
| 6,080,488 | A | 6/2000 | Hostettler et al. ........ 428/423.3 |
| 6,090,134 | A | 7/2000 | Tu et al. |
| 6,096,070 | A | 8/2000 | Ragheb et al. ................. 623/1 |
| 6,096,396 | A | 8/2000 | Patton et al. |
| 6,096,798 | A | 8/2000 | Luthra et al. |
| 6,096,809 | A | 8/2000 | Lorcks et al. |
| 6,099,562 | A | 8/2000 | Ding et al. ................. 623/1.46 |
| 6,099,563 | A | 8/2000 | Zhong |
| 6,110,188 | A | 8/2000 | Narciso, Jr. ................. 606/153 |
| 6,110,483 | A | 8/2000 | Whitbourne et al. ........ 424/423 |
| 6,113,629 | A | 9/2000 | Ken .......................... 623/1.1 |
| 6,120,536 | A | 9/2000 | Ding et al. ................. 623/1.43 |
| 6,120,904 | A | 9/2000 | Hostettler et al. ........ 428/423.3 |
| 6,121,027 | A | 9/2000 | Clapper et al. ............. 435/180 |
| 6,124,045 | A | 9/2000 | Soda et al. |
| 6,129,761 | A | 10/2000 | Hubbell ........................ 623/11 |
| 6,153,252 | A | 11/2000 | Hossainy et al. ............. 427/2.3 |
| 6,165,212 | A | 12/2000 | Dereume et al. .......... 623/1.13 |
| 6,179,817 | B1 | 1/2001 | Zhong |
| 6,197,051 | B1 | 3/2001 | Zhong |
| 6,203,551 | B1 | 3/2001 | Wu ............................ 606/108 |
| 6,214,901 | B1 | 4/2001 | Chudzik et al. ............. 523/113 |
| 6,224,894 | B1 | 5/2001 | Jamiolkowski et al. ..... 424/426 |
| 6,231,590 | B1 | 5/2001 | Slaikeu et al. ............. 606/200 |
| 6,242,041 | B1 | 6/2001 | Katoot et al. ............. 427/2.24 |
| 6,254,632 | B1 | 7/2001 | Wu et al. .................. 623/1.15 |
| 6,258,121 | B1 | 7/2001 | Yang et al. ................. 623/1.46 |
| 6,262,034 | B1 | 7/2001 | Mathiowitz et al. .......... 514/44 |
| 6,273,913 | B1 * | 8/2001 | Wright et al. ............... 623/1.42 |
| 6,299,604 | B1 | 10/2001 | Ragheb et al. |
| 6,319,520 | B1 | 11/2001 | Wuthrich et al. ........... 424/482 |
| 6,344,035 | B1 | 2/2002 | Chudzik et al. ............. 604/265 |
| 6,362,271 | B1 | 3/2002 | Lin et al. |
| 6,408,878 | B2 | 6/2002 | Unger et al. |
| 6,410,612 | B1 | 6/2002 | Hatanaka |
| 6,464,683 | B1 | 10/2002 | Samuelson et al. |
| 6,503,556 | B2 | 1/2003 | Harish et al. |
| 6,545,097 | B2 | 4/2003 | Pinchuk et al. |
| 6,551,708 | B2 | 4/2003 | Tsuda et al. |
| 6,716,444 | B1 * | 4/2004 | Castro et al. ............... 424/422 |
| 6,746,773 | B2 | 6/2004 | Llanos et al. |
| 6,939,376 | B2 * | 9/2005 | Shulze et al. ............... 623/1.42 |
| 2001/0014717 | A1 | 8/2001 | Hossainy et al. ............. 525/60 |
| 2001/0029351 | A1 | 10/2001 | Falotico et al. |
| 2002/0051730 | A1 | 5/2002 | Bodnar et al. |
| 2002/0090389 | A1 | 7/2002 | Humes et al. |
| 2002/0094440 | A1 | 7/2002 | Llanos et al. ............... 428/421 |
| 2002/0099438 | A1 * | 7/2002 | Furst ........................ 623/1.16 |
| 2002/0111590 | A1 | 8/2002 | Davila et al. ............... 604/265 |
| 2002/0122877 | A1 | 9/2002 | Harish et al. |
| 2002/0123801 | A1 | 9/2002 | Pacetti et al. |
| 2002/0133183 | A1 | 9/2002 | Lentz et al. |
| 2002/0143386 | A1 | 10/2002 | Davila et al. |
| 2002/0165608 | A1 | 11/2002 | Llanos et al. |
| 2002/0188037 | A1 | 12/2002 | Chudzik et al. |
| 2003/0004563 | A1 | 1/2003 | Jackson et al. |
| 2003/0031780 | A1 | 2/2003 | Chudzik et al. |
| 2003/0039689 | A1 | 2/2003 | Chen et al. |
| 2003/0060877 | A1 | 3/2003 | Falotico et al. |
| 2003/0065346 | A1 | 4/2003 | Evens et al. |
| 2003/0065377 | A1 | 4/2003 | Davila et al. |
| 2003/0073961 | A1 | 4/2003 | Happ |
| 2003/0077312 | A1 | 4/2003 | Schmulewicz et al. |
| 2004/0102758 | A1 | 5/2004 | Davila et al. |

FOREIGN PATENT DOCUMENTS

| | | |
|---|---|---|
| EP | 0568310 A1 | 11/1993 |
| EP | 0623354 A1 | 11/1994 |
| EP | 0633032 A1 | 1/1995 |
| EP | 0 665 023 | 8/1995 |
| EP | 0747069 A2 | 12/1996 |
| EP | 0815803 A1 | 1/1998 |
| EP | 0893108 A2 | 1/1999 |
| EP | 0950385 A2 | 10/1999 |
| EP | 0950386 A2 | 10/1999 |
| EP | 0 970 711 | 1/2000 |
| EP | 0968688 A1 | 1/2000 |
| EP | 0997115 A2 | 5/2000 |
| EP | 1 023 879 | 8/2000 |
| EP | 1 192 957 | 4/2002 |
| WO | WO 92/05695 | 4/1992 |
| WO | WO 92/18320 | 10/1992 |
| WO | WO 94/02185 | 2/1994 |
| WO | WO 96/21404 | 7/1996 |
| WO | WO 97/41164 | 11/1997 |
| WO | WO 98/08463 | 3/1998 |
| WO | WO 98/13405 | 4/1998 |
| WO | WO 98/36784 | 8/1998 |
| WO | WO 98/58680 | 12/1998 |
| WO | WO 99/32051 | 7/1999 |
| WO | WO 99/55396 | 11/1999 |
| WO | WO 00/02599 | 1/2000 |
| WO | WO 00/12147 | 3/2000 |
| WO | WO 00/27455 | 5/2000 |
| WO | WO 00/29043 | 5/2000 |
| WO | WO 00/32255 | 6/2000 |
| WO | WO 00/38754 | 7/2000 |
| WO | WO 00/41738 | 7/2000 |
| WO | WO 00/64506 | 11/2000 |
| WO | WO 01/01890 | 1/2001 |
| WO | WO 01/30403 A1 | 5/2001 |
| WO | WO 01/49340 | 7/2001 |
| WO | WO 01/87342 A2 | 11/2001 |
| WO | WO 01/87368 | 11/2001 |
| WO | WO 01/87372 | 11/2001 |
| WO | WO 01/87376 A1 | 11/2001 |
| WO | WO 02/24249 | 3/2002 |
| WO | WO 02/26139 A1 | 4/2002 |
| WO | WO 02/26271 A | 4/2002 |
| WO | WO 02/26281 A1 | 4/2002 |
| WO | WO 02/47732 | 6/2002 |
| WO | WO 03/022324 | 3/2003 |

OTHER PUBLICATIONS

Novick et al., Protein-Containing Hydrophobic Coatings and Films, Biomaterials (2001), vol. Date 2002, 23 (2), pp. 441-448.
U.S. Appl. No. 09/966,036, filed Sep. 28, 2001, Happ.
U.S. Appl. No. 10/176,510, filed Jun. 21, 2001, Hossainy et al.
U.S. Appl. No. 10/177,117, filed Jun. 21, 2002, Hossainy.
U.S. Appl. No. 10/177,154, filed Jun. 21, 2002, Hossainy et al.
U.S. Appl. No. 10/198,912, filed Jul. 19, 2002, Ding et al.
U.S. Appl. No. 10/251,111, filed Sep. 19, 2002, Hossainy et al.
U.S. Appl. No. 10/320,899, filed Dec. 16, 2002, Shah et al.
U.S. Appl. No. 10/376,348, filed Feb. 26, 2003, Ding et al.
U.S. Appl. No. 10/428,691, filed May 1, 2003, Pacetti.
U.S. Appl. No. 10/931,927, filed Aug. 31, 2004, Pacetti.
Arnold et al., Effects of environment on the creep properties of a poly (ethylmethacrylate) based bone cement J. Mater. Sci: Mater. In Med., vol. 12, pp. 707-717 (2001).
Bellex International, *CYTOP®, Amorphous Fluorocarbon Polymer*, 1 page, no date.
Bellex International, *Selected CYTOP Physical Data*, 1 page, no date.
Bellex International, *CYTOP®*, http://www.bellexinternational.com/cytop.htm, printed Mar. 30, 2001, 1 page.
Cifková et al., Irritation effects of residual products derived from p(HEMA) gels, Biomaterials, vol. 9, (Jul. 1998), pp. 372-375.
Dalsin et al., DOPA: A New Anchor for PEGylation of Biomaterial Surfaces, Soc. For Biomaterials 28th Annual Meeting Transactions, pp. 40 (2002).
Deb et al., Effect of crosslinking agents on poly(ethylmethacrylate) bone cements, J. of Mater.Sci: Mater. In Med., vol. 8, pp. 829-833 (1997).

Del Guerra et al., In vitro biocompatibility of fluorinated polyurethanes, J. Mater. Sci. in Med., vol. 5, pp. 452-456 (1994).

DuPont, Teflon AF 1601S amorphous fluoropolymer solutions, product information, 2 pages (1998).

DuPont, Processing of Teflon® AF, Teflon Amorphous Fluoropolymer, http://www.dupont.com/teflon/af/processing.html, printed Mar. 30, 2001, 1 page.

DuPont, High-Performance/Potential Applications, Teflon Amorphous Fluoropolymer, http://www.dupont.com/teflon/af/potapps.html, printed Mar. 30, 2001, 3 pages.

DuPont, Performance Comparison of Teflon AF, Teflon Amorphous Fluoropolymer, http://www.dupont.com/teflon/af/performance.html, printed Mar. 30, 2001, 3 pages.

DuPont, Unique Properties of Teflon® AF, Teflon Amorphous Fluoropolymer, http://www.dupont.com/teflon/af/unique.html, printed Mar. 30, 2001, 3 pages.

DuPont, Teflon® AF: A New Generation of High-Performance Fluoropolymer Resins, http://www.dupont.com/teflon/af/index.html, printed Mar. 30, 2001, 1 page.

DuPont, Teflon® Protects Superconductors Against Acid, Teflon Amorphous Fluoropolymer, http://www.dupont.com/teflon/af/superconductor.html, printed Sep. 21, 2004, 2 pages.

DuPont, Available Grades of DuPont Teflon® AF, Teflon Amorphous Fluoropolymer, http://www.dupont.com/teflon/af/grades.html, printed Sep. 21, 2004, 2 pages.

DuPont, Teflon® AF amorphous fluoropolymers, Product Information, 6 pages (1998).

DuPont, Sales Notice, Teflon Amorphous Fluoropolymer, http://www.dupont.com/teflon/af/patent.html, printed Sep. 21, 2004, 2 pages.

Fine et al., Improved nerve regeneration through piezoelectric vinylidenefluoride- trifluoroethylene copolymer guidance channels, Biomaterials, vol. 12, Oct., pp. 775-780 (1991).

Fischell, Polymer Coatings for Stents, Circulation, 94:1494-95 (1996).

Gullickson, Reference Data Sheet on Common Chlorinated Solvents, http://www.mcs.net/~hutter/tee/chlorina.html, printed Mar. 30, 2001, 5 pages.

Gunn et al., Stent coatings and local drug delivery, Eur. Heart J., vol. 20, issue 23, pp. 1693-1700 (1999).

Harper et al., Fatigue Characteristics of Polyethylmethacrylate Based Bone Cement Reinforced with Silane Coupled Hydroxyapatite, Fifth World Biomaterials Congress, May 29-Jun. 2, 1996, Toronto, Canada, Abstract 351, 3 pgs.

Harper et al., Mechanical properties of hydroxyapatite reinforced poly (ethyl methacrylate) bone cement after immersion in a physiological solution: influence of a silane coupling agent, J. Mater. Sci.: Mater. In Med., vol. 11, pp. 491-497 (2000).

Kruft et al., Studies on radio-opaque polymeric biomaterials with potential applications to endovascular prostheses, Biomaterials, vol. 17, No. 18, pp. 1803-1812 (1996).

Lambert et al., Localized Arterial Wall Drug Delivery From a Polymer-Coated Removable Metallic Stent, Circulation, vol. 90, No. 2, pp. 1003-1011 (1994).

Laroche et al., Polyvinylidene fluoride (PVDF) as a biomaterial: From polymeric raw material to monofilament vascular suture, J. of Biomedical Mat. Research, vol. 29, pp. 1525-1536 (1995).

Lin et al., Fluropolymer Alloys Performance Optimization of PVDF Alloys, Fluropolymers 2 Properties, edited by Hougham et al., Plenum Publishers N.Y. pp. 121-136 (1999).

Lin et al., Surface characterization and platelet adhesion studies on fluorocarbons prepared by plasma-induced graft polymerization, J. Biomater Sci. Polymer Edn., vol. 11, No. 7, pp. 701-714 (2000).

Luthra, Biointeractions Ltd (BIL), http://www.biomateria.com/biointeractions.html, printed Sep. 21, 2004, 3 pages.

3M, Specialty Fluids 3M™ Fluorinert™ Liquids, Typical Properties, http://www.3m.com/market/industrial/fluids/fluoprop.html, printed Mar. 30, 2001, 3 pages.

Materials Engineering, Applications in Design/Manufacturing/R&D, Materials Selector 1993, Penton Publishing (1992) 6 pgs.

Medtronic, Trillium Affinity NT, Oxygenator, Product Information, 6 pages (2000).

NCMS SOLV-DB, Query Results for: CFC, http://solvdb.ncms.org/CAT01.idc?chemcat=CFC, printed Mar. 30, 2001, 2 pages.

NCMS SOLV-DB, Query Results for: FC-75 Fluorinert, http://solvdb.ncms.org/common01.idc, printed Mar. 30, 2001, 2 pages.

Parkell, Inc., SNAP Powder-Liquid Temporary Crown and Bridge Resin, http://www.parkell.com/snap.html, printed Oct. 21, 2004, 1 pg.

Parkell, Inc., Material Safety Data Sheets, http://www.parkell.com/msds.html, printed Oct. 21, 2004, 2 pgs.

Parkell, Inc., MSDS No: S426, VAR, Material Safety Data Sheet, 2 pgs (2002).

Parkell, Inc., MSDS No: S441, Material Safety Data Sheet, 2 pgs (2002).

Porté-Durrieu et al., Surface Treatment of Biomaterials by Gamma and Swift Heavy Ions Grafting, Nuclear Instruments and Methods in Physics Research, vol. B 151, pp. 404-415 (1999).

Porté-Durrieu et al., Development of "Heparin-Like" Polymers Using Swift Heavy Ion and Gamma Radiation. I. Preparation and Characterization of the Materials, Surface Treatment of Biomaterials, pp. 119-127 (2000).

Revell et al., Experimental Studies of the Biological Response to a New Bone Cement: II Soft Tissue Reactions in the Rat, Clinical Materials, vol. 10, pp. 233-238 (1992).

Techspray, Bulk Solvents, http://www.techspray.com/bulksup.htm, printed Sep. 21, 2004, 3 pages.

Techspray, Flux Remover AMS, Product Information, http://www.techspray.com/1665info.htm, printed Aug. 28, 2001, 2 pages.

Teomin et al., Perivascular delivery of heparin for the reduction of smooth muscle cell proliferation after endothelial injury, J. of Controlled Release, vol. 60, pp. 129-142 (1999).

Topol et al., Frontiers in Interventional Cardiology, Circulation, vol. 98, pp. 1802-1820 (1998).

Urban et al., Why Make Monofilament Sutures Out of Polyvinylidene Fluoride?, ASAIO J., vol. 40, No. 2, pp. 145-156 (1994).

Verweire et al. Evaluation of fluorinated polymers as coronary stent coating, J. Mater.Sci: Mater. In Med., vol. 11, No. 4, pp. 207-212 (2000).

Weightman et al., The Mechanical Properties of Cement and Loosening of the Femoral Component of Hip Replacements, J. Bone and Joint Surg., vol. 69-B, No. 4, pp. 558-564 (Aug. 1987).

Wholey et al., Global Experience in Cervical Carotid Artery Stent Placement, Catherization and Cardiovascular Inteventions, vol. 50, No. 2, pp. 160-167 (2000).

Woo et al., Phase Behavior of Polycarbonate Blends with Selected Halogenated Polymers, J. Appl. Polym. Sci., vol. 30, pp. 4243-4249 (1985).

International Search Report for PCT appl. PCT/US03/15347, filed May 14, 2003, date of mailing Sep. 4, 2003, 6 pgs.

International Search Report for PCT appl. PCT/US03/28643, filed Sep. 10, 2003, date of mailing Mar. 12, 2003, 10 pgs.

International Search Report for PCT appl. PCT/US03/21170, filed Jul. 2, 2003, date of mailing Oct. 31, 2003, 8 pgs.

* cited by examiner

POLYACRYLATES COATINGS FOR IMPLANTABLE MEDICAL DEVICES

CROSS REFERENCE

This is a continuation-in-part of U.S. patent application Ser. No. 09/894,293, filed on Jun. 27, 2001, now abandoned.

BACKGROUND OF THE INVENTION

1. Field of the Invention

This invention is directed to coatings for implantable medical devices, such as drug eluting vascular stents.

2. Description of Related Art

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress against the atherosclerotic plaque of the lesion to remodel the lumen wall. The balloon is then deflated to a smaller profile to allow the catheter to be withdrawn from the patient's vasculature.

A problem associated with the above procedure includes formation of intimal flaps or torn arterial linings which can collapse and occlude the conduit after the balloon is deflated. Moreover, thrombosis and restenosis of the artery may develop over several months after the procedure, which may require another angioplasty procedure or a surgical by-pass operation. To reduce the partial or total occlusion of the artery by the collapse of arterial lining and to reduce procedure, which may require another angioplasty procedure or a surgical by-pass operation. To reduce the partial or total occlusion of the artery by the collapse of arterial lining and to reduce the chance of the development of thrombosis and restenosis, a stent is implanted in the lumen to maintain the vascular patency.

Stents are used not only as a mechanical intervention but also as a vehicle for providing biological therapy. As a mechanical intervention, stents act as scaffoldings, functioning to physically hold open and, if desired, to expand the wall of the passageway. Typically, stents are capable of being compressed, so that they can be inserted through small vessels via catheters, and then expanded to a larger diameter once they are at the desired location. Examples in patent literature disclosing stents which have been applied in PTCA procedures include stents illustrated in U.S. Pat. No. 4,733,665 issued to Palmaz, U.S. Pat. No. 4,800,882 issued to Gianturco, and U.S. Pat. No. 4,886,062 issued to Wiktor.

Biological therapy can be achieved by medicating the stents. Medicated stents provide for the local administration of a therapeutic substance at the diseased site. In order to provide an efficacious concentration to the treated site, systemic administration of such medication often produces adverse or toxic side effects for the patient. Local delivery is a preferred method of treatment in that smaller total levels of medication are administered in comparison to systemic dosages, but are concentrated at a specific site. Local delivery thus produces fewer side effects and achieves more favorable results. One proposed method for medicating stents involves the use of a polymeric carrier coated onto the surface of a stent. A solution which includes a solvent, a polymer dissolved in the solvent, and a therapeutic substance dispersed in the blend is applied to the stent. The solvent is allowed to evaporate, leaving on the stent surface a coating of the polymer and the therapeutic substance impregnated in the polymer. The embodiments of the invention provide coatings for implantable devices, such as stents, and methods of coating the same.

SUMMARY

A coating for an implantable medical device is provided, the coating comprises a thermoplastic polyacrylate material free from acetate species and a therapeutically active agent incorporated therein. The polyacrylate material can include homopolymers, copolymers or terpolymers of alkylacrylates or alkylmethacrylates, and blends thereof. The polyacrylate material can be poly(n-butyl methacrylate). The polyacrylate material can include non-acrylate polymers such as fluorinated polymers or poly(ethylene-co-vinyl alcohol).

According to another embodiment of this invention, a coating for an implantable medical device is provided, the coating comprises a first layer having an active agent incorporated therein and a second layer disposed over the first layer, wherein the second layer comprises a thermoplastic polyacrylate material for modifying the rate of release of the agent.

According to yet another embodiment of the invention, a method of coating an implantable medical device is provided, the method comprises depositing a first layer on the device, the first layer including an active agent for the sustained release of the agent, and depositing a second layer over the first layer, the second layer comprising a thermoplastic polyacrylate material for modifying the rate of release of the agent.

DETAILED DESCRIPTION

Figure 1:
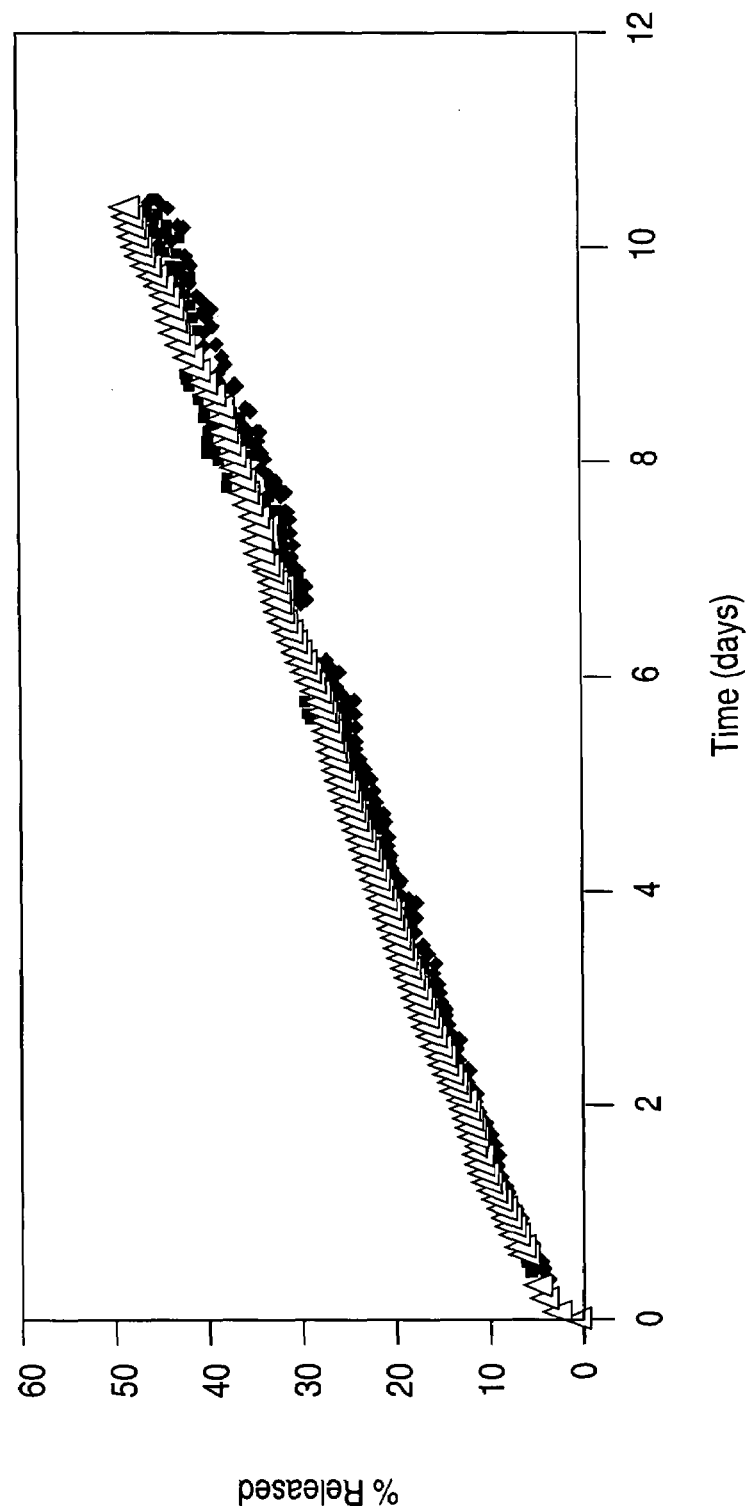
FIGS. 1 and 2 are graphs illustrating a profile of a rate of release of a drug from stents coated according to a method of the present invention.

A coating for an implantable medical device, such as a stent, according to one embodiment of the present invention, can include a drug-polymer layer, an optional topcoat layer, and an optional primer layer. The drug-polymer layer can be applied directly onto the stent surface to serve as a reservoir for a therapeutically active agent or drug which is incorporated into the drug-polymer layer. The topcoat layer, which can be essentially free from any therapeutic substances or drugs, serves as a rate limiting membrane which further controls the rate of release of the drug. The optional primer layer can be applied between the stent and the drug-polymer layer to improve the adhesion of the drug-polymer layer to the stent.

According to one embodiment of the present invention, polymers of esters having the general formula (I)

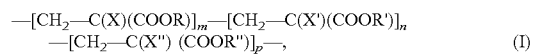

$$-[CH_2-C(X)(COOR)]_m-[CH_2-C(X')(COOR')]_n-[CH_2-C(X'')(COOR'')]_p-, \quad (I)$$

or blends thereof, can be used for making the stent coatings.

In formula (I), X, X', and X" is each, independently, a hydrogen atom (acrylates) or an alkyl group, such as a methyl group $CH_3$ (methacrylates); R, R' and R" is each, independently, a $C_1$ to $C_{12}$ straight chained or branched aliphatic radical; "m" is an integer larger than 1, and "n" and "p" is each 0 or an integer. If both n=0 and p=0, the polymer of formula (I) is a homopolymer (i.e., PBMA). If n≠0 and p=0, or n=0 and p≠0, the polymer of formula (I) is a copolymer, and if n≠0 and p≠0, the polymer of formula (I) is a terpolymer.

Polymers of formula (I) can be used for making either the drug-polymer layer, the topcoat membrane, the optional primer layer, or any combination thereof. For the purposes of the present invention, such polymers, or blends thereof, are defined as "polyacrylates" or as "polyacrylate materials."

One example of a polyacrylate suitable for fabricating either the drug-polymer layer or the topcoat membrane is poly(n-butyl methacrylate) (PBMA), described by formula (I) where $X=CH_3$, n=0, p=0, and "R" is a n-butyl radical $C_4H_9$ ($-CH_2-CH_2-CH_2-CH_3$). PBMA has good biocompatibility, is soluble in many common solvents, has good mechanical and physical properties, and adheres well to the underlying stent surface or the primer layer. PBMA is available commercially from Aldrich Chemical Co. of Milwaukee, Wis., and from Esschem, Inc. of Lynwood, Pa.

The rate of release of the drug through the polymer, such as the topcoat membrane, is related to the rate of diffusion of the drug through the matrix. The slower the rate of diffusion, the greater the polymer's ability to prolong the rate of release and the residence time of the drug at the implantation site. The rate of diffusion is in turn related to the water adsorption rate, the degree of crystallinity, if any, and the glass transition temperature ($T_g$) of the polymer.

As a general rule, the more water the polymer absorbs at body temperature, the faster the drug diffuses out of the polymer, and the greater the degree of crystallinity in the polymer's structure, the slower a drug will diffuse out of the polymer. Since all of the R, R' and R" groups in these polyacrylates are aliphatic, water adsorption tends to be low. One common technique for producing these polymers is by free radical polymerization yielding amorphous polymers with no crystallinity. Hence, it is the glass transition temperature that is one of the important discriminating characteristic for these polymers.

Consequently, the present invention allows manipulating the rate of release of the drug into the blood stream by varying $T_g$ of the polymer or the blend of polymers forming the drug-polymer layer and/or the membrane. Typically, it is desirable to decrease the rate of release. In order to do so, the polyacrylates having higher values of $T_g$ can be used. Examples of such polyacrylates include poly(methyl methacrylate) ($T_g=105°$ C.) and poly(tert-butyl methacrylate) ($T_g=107°$ C.).

However, if it is desirable to increase the rate of release, the polyacrylates having low values of $T_g$ can be used. PBMA is one of such polyacrylates having the $T_g$ of about 20° C. Examples of other suitable polyacrylates having low $T_g$ include poly(n-hexyl methacrylate) ($T_g=-5°$ C.) and poly(methyl acrylate) ($T_g=9°$ C.).

For a copolymer of these polyacrylates, the Tg (on the Kelvin scale) is generally the mass-fraction weighted average of the constituent components of the copolymer. Consequently, a copolymer or terpolymer of formula (I) with predetermined higher or lower value of $T_g$ can be used as a drug-polymer layer and/or a topcoat membrane, thus providing a desirable lower or higher rate of release of the drug, respectively. For example, a random poly(methyl methacrylate-co-n-butyl methacrylate) [P(MMA-BMA)], having about 30 molar percent of methyl-methacrylate-derived units and about 70 molar percent of n-butyl-methacrylate-derived units, has a theoretical $T_g$ of about 45.50° C. Therefore, a topcoat membrane made of P(MMA-BMA) will provide faster drug release than pure PMMA but slower than pure PBMA. Similarly, blends of individual polyacrylates, e.g., PBMA and PMMA can be used.

Some examples of polyacrylates that are suitable for fabrication of the coating, e.g., the drug-polymer layer and/or the topcoat membrane, are summarized in Table 1.

TABLE 1

Examples of Polyacrylates $-[CH_2-C(X)(COOR)]_m-[CH_2-C(X')(COOR')]_n-$
Suitable for Fabricating Stent Coatings

| No. | Polyacrylate | Abbreviation | R | X | m | R' | X' | n | $T_g$, ° C. |
|---|---|---|---|---|---|---|---|---|---|
| 1 | Poly(n-butyl methacrylate) | PBMA | n-C₄H₉ | CH₃ | >1 | N/A | N/A | 0 | 20 |
| 2 | Poly(iso-butyl methacrylate) | Pi-BMA | i-C₄H₉ | CH₃ | >1 | N/A | N/A | 0 | 66 |
| 3 | Poly(tert-butyl methacrylate) | PBMA | tert-C₄H₉ | CH₃ | >1 | N/A | N/A | 0 | 107 |
| 4 | Poly(methyl methacrylate) | PMMA | CH₃ | CH₃ | >1 | N/A | N/A | 0 | 105 |
| 5 | Poly(ethyl methacrylate) | PEMA | C₂H₅ | CH₃ | >1 | N/A | N/A | 0 | 63 |
| 6 | Poly(n-propyl methacrylate) | PPMA | n-C₃H₇ | CH₃ | >1 | N/A | N/A | 0 | 35 |
| 7 | Poly(methyl acrylate) | PMA | CH₃ | H | >1 | N/A | N/A | 0 | 9 |
| 8 | Poly(n-hexyl methacrylate) | PHMA | n-C₆H₁₃ | CH₃ | >1 | N/A | N/A | 0 | -5 |
| 9 | Poly(methyl methacrylate-co-n-butyl methacrylate) | P(MMA-BMA) | CH₃ | CH₃ | 30 | n-C₄H₉ | CH₃ | 70 | 46 |
| 10 | Poly(n-butyl methacrylate-co-iso-butyl methacrylate) | P(BMA-i-BMA) | n-C₄H₉ | CH₃ | 50 | i-C₄H₉ | CH₃ | 50 | 35 |

Only homo- and copolymers are listed in Table 1 (that is, the polymers of formula (I) where p=0), but it should be understood that terpolymers corresponding to formula (I) (when n≠0 and p≠0) can be used as well.

To fabricate the coating, one of the polyacrylates, or a blend thereof can be applied on the stent using commonly used techniques known to those having ordinary skill in the art. For example, the polyacrylate can be applied to the stent by dissolving the polymer in a solvent, or a mixture of solvents, and applying the resulting solution on the stent by spraying or immersing the stent in the solution.

Representative examples of some suitable solvents include N,N-dimethylacetamide (DMAC), N,N-dimethylformamide (DMF), tethrahydrofurane (THF), cyclohexanone, xylene, toluene, acetone, methyl ethyl ketone, propylene glycol monomethyl ether, methyl butyl ketone, ethyl acetate, n-butylacetate, and dioxane. Examples of suitable mixtures of solvents include mixtures of DMAC and methanol (e.g., a 50:50 by mass mixture), cyclohexanone and acetone (e.g., 80:20, 50:50, 20:80 by mass mixtures), acetone and xylene (e.g. a 50:50 by mass mixture), and acetone, FLUX REMOVER AMS, and xylene (e.g., a 10:50:40 by mass mixture). FLUX REMOVER AMS is trade name of a solvent manufactured by Tech Spray, Inc. of Amarillo, Tex. comprising about 93.7% of a mixture of 3,3-dichloro- 1,1,1,2,2-pentafluoropropane and 1,3-dichloro-1,1,2,2,3-pentafluoropropane, and the balance methanol, with trace amounts of nitromethane.

In addition, blends of polyacrylates with polymers other than polyacrylates can be used to fabricate the coating. In one embodiment, the blend of polyacrylates with non-acrylate materials is free from acetate species. Poly(ethylene-co-vinyl alcohol) (EVAL) is one example of a suitable non-acrylate polymer. EVAL has the general formula —[CH$_2$—CH$_2$]$_q$—[CH$_2$—CH(OH)]$_r$—, where "q" and "r" is each an integer. EVAL may also include up to 5 molar % of units derived from styrene, propylene and other suitable unsaturated monomers. A brand of copolymer of ethylene and vinyl alcohol distributed commercially under the trade name EVAL by Aldrich Chemical Co., or manufactured by EVAL Company of America of Lisle, Ill., can be used.

Examples of other polymers with which polyacrylates can be blended include fluorinated polymers, such as poly(vinylidene fluoride) (PVDF) and poly(vinylidene fluoride-co-hexafluoro propene) (PVDF-HFP). The blend of a polyacrylate and a fluorinated polymer can contain between about 10 and about 95% (mass) of the fluorinated polymer.

The polyacrylates can be used to manufacture the primer layer, drug-polymer layer, topcoat membrane, or all three layers. For example, the polyacrylates can be used to make both the drug-polymer layer and the topcoat membrane, but not the primer layer. Any combination of the three layers can include a polyacrylate, so long as at least one of the layers includes the material. If a polyacrylate is used to make only one of the layers, the other layer or layers can be made of an alternative polymer.

Representative examples of suitable alternative polymers include EVAL, poly(hydroxyvalerate), poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-co-trimethylene carbonate), polyphosphoester, polyphosphoester urethane; poly(amino acids), cyanoacrylates, poly(trimethylene carbonate), poly(iminocarbonate), co-poly(ether-esters) (e.g. PEO/PLA), polyalkylene oxalates, polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene fluoride and polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, and ethylene-vinyl acetate copolymers), polyamides (such as Nylon 66 and polycaprolactam), alkyd resins, polycarbonates, polyoxymethylenes, polyimides, polyethers, epoxy resins, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose.

The coating of the present invention has been described in conjunction with a stent. However, the coating can also be used with a variety of other medical devices. Examples of the implantable medical device, that can be used in conjunction with the embodiments of this invention include stent-grafts, grafts (e.g., aortic grafts), artificial heart valves, cerebrospinal fluid shunts, pacemaker electrodes, axius coronary shunts and endocardial leads (e.g., FINELINE and ENDOTAK, available from Guidant Corporation). The underlying structure of the device can be of virtually any design. The device can be made of a metallic material or an alloy such as, but not limited to, cobalt-chromium alloys (e.g., ELGILOY), stainless steel (316L), "MP35N," "MP20N," ELASTINITE (Nitinol), tantalum, tantalum-based alloys, nickel-titanium alloy, platinum, platinum-based alloys such as, e.g., platinum-iridium alloy, iridium, gold, magnesium, titanium, titanium-based alloys, zirconium-based alloys, or combinations thereof. Devices made from bioabsorbable or biostable polymers can also be used with the embodiments of the present invention.

"MP35N" and "MP20N" are trade names for alloys of cobalt, nickel, chromium and molybdenum available from Standard Press Steel Co. of Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

The active agent or the drug can include any substance capable of exerting a therapeutic or prophylactic effect for a patient. The drug may include small molecule drugs, peptides, proteins, oligonucleotides, and the like. The active agent could be designed, for example, to inhibit the activity of vascular smooth muscle cells. It can be directed at inhibiting abnormal or inappropriate migration and/or proliferation of smooth muscle cells to inhibit restenosis. Examples of drugs include antiproliferative substances such as actinomycin D, or derivatives and analogs thereof. Synonyms of actinomycin D include dactinomycin, actinomycin IV, actinomycin I$_1$, actinomycin X$_1$, and actinomycin C$_1$. The active agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel, docetaxel, methotrexate, azathioprine, vincristine, vinblastine, fluorouracil, doxorubicin, hydrochloride, and mitomycin. Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin. Examples of such cytostatic or antiproliferative agents include angiopeptin, angiotensin converting enzyme inhibitors such as captopril, cilazapril or lisinopril, calcium channel blockers (such as nifedipine), colchicine, fibroblast growth factor (FGF) antagonists, fish oil (ω-3-fatty acid), histamine antagonists, lovastatin (an inhibitor of HMG-CoA reductase, a cholesterol lowering drug), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon; genetically engineered epithelial cells; rapamycin and structural derivatives or functional analogs thereof, such as 40-O-(2-hydroxy)ethyl-rapamycin (known by the trade name of Everolimus available from Novartis) 40-O-(3-hydroxy)propyl-rapamycin and 40-O-[2-(2-hydroxy)ethoxy]ethyl-rapamycin; tacrolimus; and dexamethasone.

EXAMPLES

Some embodiments of the present invention are illustrated by the following Examples.

Example 1

A polymer solution containing between about 0.1 mass % and about 15 mass %, for example, about 2.0 mass % of EVAL and the balance, DMAC solvent, can be prepared. The solution can be applied onto a stent to form a primer layer. To apply the primer layer, a spray apparatus, such as an EFD 780S spray nozzle with a VALVEMATE 7040 control system, manufactured by EFD, Inc. of East Providence, R.I. can be used. The EFD 780S spray nozzle is an air-assisted external mixing atomizer. The composition is atomized by air and applied to the stent surfaces. During the process of applying the composition, the stent can be optionally rotated about its longitudinal axis, at a speed of 50 to about 150 rpm. The stent can also be linearly moved along the same axis during the application.

The EVAL solution can be applied to a 13-mm TETRA stent (available from Guidant Corporation) in a series of 10-second passes, to deposit, for example, 10 μg of coating per spray pass. Instead of the 13-mm TETRA stent, another suitable stent can be used, for example, a 12-mm VISION stent (also available from Guidant Corporation). Between the spray passes, the stent can be dried for about 10 seconds using flowing air with a temperature of about 60° C. Five spray passes can be applied, followed by baking the primer layer at about 140° C. for one hour. As a result, a primer layer can be formed having a solids content of about 50 μg. "Solids" means the amount of the dry residue deposited on the stent after all volatile organic compounds (e.g., the solvent) have been removed.

A drug-containing formulation can be prepared comprising:

(a) between about 0.1 mass % and about 15 mass %, for example, about 2.0 mass % of EVAL;

(b) between about 0.1 mass % and about 2 mass %, for example, about 1.0 mass % of an active agent, for example, Everolimus; and (c) the balance, a solvent mixture of DMAC and pentane, the solvent mixture containing about 80 (mass) % of DMAC and about 20 (mass) % of pentane.

In a manner identical to the application of the primer layer, five spray passes can be performed, followed by baking the drug-polymer layer at about 50° C. for about 2 hours, to form the drug-polymer layer having a solids content between about 30 μg and 750 μg, for example, about 90 μg, and a drug content of between about 10 μg and about 250 μg, for example, 30 μg.

Finally, a topcoat composition to control the drug release rate can be prepared, comprising between about 0.1 mass % and about 15 mass %, for example, about 2.0 mass % PBMA and the balance a solvent system, for example, a solvent system including a 10:50:40 (mass) blend of acetone, Techspray's FLUX REMOVER AMS, and xylene. In a manner identical to the application of the primer layer and the drug-polymer layer, a number of spray passes are performed followed by final baking at about 50° C. for about 2 hours. As a result, the topcoat membrane can be formed, the membrane having a solids content of between about 30 μg and about 350 μg, for example, about 50 μg.

Example 2

A stent was coated as described in Example 1, except instead of the Everolimus, estradiol was used. The coated stent was tested for a study of the drug release. The stent was immersed for 24 hours in bovine serum. The drug was extracted, and the amount of estradiol released after 24 hours was measured chromatographically (by HPLC). The results of this study are summarized in Table 2.

TABLE 2

Drug Release Study of Stent Coatings Having PBMA Topcoat Membranes (EVAL-based Drug-Polymer Layer, Estradiol Drug)

| No. | Topcoat Membrane Solids, μg | Drug Loaded in the Drug-Polymer Layer, μg | % of the Drug Released in 24 Hours |
|---|---|---|---|
| 1 | 30 | 240 | 15.0 |
| 2 | 50 | 240 | 13.0 |
| 3 | 100 | 240 | 11.0 |
| 4 | 160 | 240 | 4.3 |
| 5 | 300 | 170 | 1.5 |

Further, a kinetic study of the drug release profile was conducted. The stent had the total amount of solids of the topcoat membrane of about 160 μg and the total amount of estradiol in the drug-polymer layer of about 30 μg. The stent was immersed in a phosphate buffered saline solution having 1 mass % of sodium dodecyl sulfate. A sample of the solution was taken every 20 minutes and analyzed by HPLC for the amount of estradiol released.

As seen from the release profile for three different coated stents shown on FIG. 1, after 10 days about 50 mass % of estradiol was released in an almost perfect linear profile indicating a topcoat layer-controlled zero-order type of release. The small burst in the first 24 hours is due to the saturation of the topcoat layer with the drug. Once a stable state was established, the release rate remained constant for 240 hours. The linear correlation coefficient between 24 and 240 hours was 0.997.

Example 3

A stent was coated as described in Example 1, except instead of Everolimus, etoposide was used. The coated stent was tested for a study of the drug release as described in Example 2. The results of this study are summarized in Table 3.

TABLE 3

Drug Release Study of Stent Coatings Having PBMA Topcoat Membranes (EVAL-based Drug-Polymer Layer, Etoposide Drug)

| No. | Topcoat Membrane Solids, μg | Topcoat Membrane Thickness, μm | Stent | Drug Loaded in the Drug-Polymer Layer, μg | Amount of the Drug Released in 24 Hours, μg | % of the Drug Released in 24 Hours |
|---|---|---|---|---|---|---|
| 1 | 30 | 0.54 | 12 mm VISION | 240 | 139 | 57.9 |
| 2 | 50 | 0.89 | 12 mm VISION | 240 | 58 | 24.2 |

TABLE 3-continued

Drug Release Study of Stent Coatings Having PBMA Topcoat
Membranes (EVAL-based Drug-Polymer Layer, Etoposide Drug)

| No. | Topcoat Membrane Solids, μg | Topcoat Membrane Thickness, μm | Stent | Drug Loaded in the Drug-Polymer Layer, μg | Amount of the Drug Released in 24 Hours, μg | % of the Drug Released in 24 Hours |
|---|---|---|---|---|---|---|
| 3 | 100 | 1.30 | 12 mm VISION | 240 | 24 | 10.0 |
| 4 | 50 | 0.61 | 13 mm TETRA | 180 | 148 | 82.2 |
| 5 | 120 | 1.46 | 13 mm TETRA | 180 | 70 | 38.9 |
| 6 | 200 | 2.44 | 13 mm TETRA | 180 | 72 | 40.0 |
| 7 | 200 | 2.44 | 13 mm TETRA | 180 | 41 | 22.7 |
| 8 | 300 | 3.86 | 13 mm TETRA | 180 | 50 | 27.8 |

Figure 2:
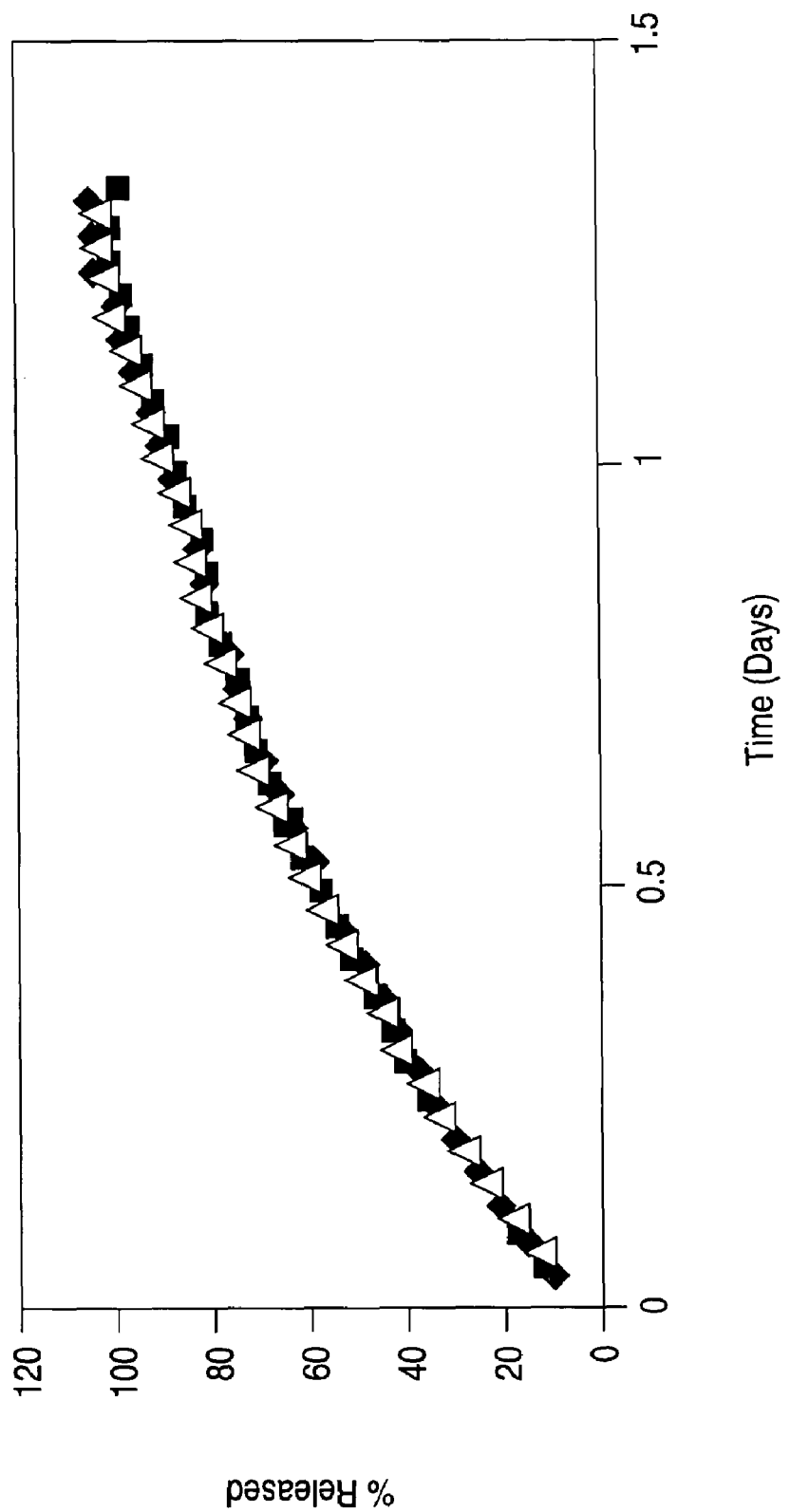

A kinetic study of the drug release profile was conducted. The stent was immersed in a phosphate-buffered saline solution having about 1 mass % of sodium dodecyl sulfate. The solution was frequently sampled and the drug concentration was measured using HPLC. The stent had the total amount of solids of the topcoat membrane of about 30 μg and the total amount of estradiol in the drug-polymer layer of about 160 μg. As seen from the release profile for three different coated stents shown on FIG. 2, the profile was close to linear and the reproducibility was excellent.

Example 4

A primer layer can be applied onto a stent as described in Example 1. A drug formulation can be prepared comprising:
(a) between about 0.1 mass % and about 15 mass %, for example, about 2.0 mass % of PBMA;
(b) between about 0.1 mass % and about 2 mass %, for example, about 1.6 mass % of a therapeutically active substance, for example, everolimus; and
(c) the balance, a solvent system, for example a 60:40 (mass) blend of acetone and xylene.

The drug containing formulation can then be applied to the stent, and a drug-polymer layer is formed, in a manner identical to that described in Example 1. The solids contents of the drug-polymer layer can be 1,200 μg.

Finally, a topcoat composition to control the drug release rate can be prepared, comprising between about 0.1 mass % and about 15 mass %, for example, about 2.0 mass % PBMA and the balance a solvent system, for example, a solvent system including a 10:50:40 (mass) blend of acetone, Techspray's FLUX REMOVER AMS and xylene, and the topcoat membrane can be formed, in a manner identical to that described in Example 1. The topcoat membrane can have a solids content of between about 20 μg and about 200 μg, for example, about 30 μg.

Example 5

A primer layer can be applied onto a 8-mm stent as described in Example 1. A drug formulation can be prepared comprising:
(a) between about 0.1 mass % and about 15 mass %, for example, about 2.0 mass % of PBMA;
(b) between about 0.1 mass % and about 2 mass %, for example, about 1.6 mass % of a therapeutically active substance, for example, Everolimus; and
(c) the balance, a solvent system, for example a 60:40 (mass) blend of acetone and xylene.

The drug formulation can then be applied onto the stent, and a drug-polymer layer is formed in a manner identical to that described in Example 1. The solids contents of the drug-polymer layer can be 1,200 μg. In this Example, the stent coating has no separate topcoat membrane.

Example 6

A primer layer can be applied onto a 8-mm stent as described in Example 1. A drug formulation can be prepared comprising:
(a) between about 0.1 mass % and about 15 mass %, for example, about 2.0 mass % of P(MMA-BMA) having a weight-average molecular weight $M_w$ of about 150,000 available from Aldrich Chemical Company under the name PBM 150;
(b) between about 0.1 mass % and about 2 mass %, for example, about 1.0 mass % of an active agent, for example, Everolimus; and
(c) the balance, a solvent system, for example a 10:50:40 (mass) blend of acetone, Techspray's FLUX REMOVER AMS and xylene.

PBM 150 contains about 79.2 mass % of units derived from BMA. The drug formulation can then be applied onto the dried primer layer, and a drug-polymer layer is formed, in a manner identical to that described in Example 1. The drug-polymer layer can have the total amount of solids of between about 300 and 600 μg, for example, about 520 μg. In this Example, the stent coating has no separate topcoat membrane.

Example 7

A primer layer and a drug-polymer layer can be applied onto a stent as described in Example 1, the drug-polymer layer having the total amount of EVAL between about 300 and 800 μg, for example, about 325 μg. A topcoat composition to control the drug release rate can be prepared, comprising between about 0.1 mass % and about 15 mass %, for example, about 2.0 mass % P(MMA-BMA) having about 66.5 mass % of units derived from BMA, and the balance of a solvent system, for example, a solvent system including a 10:50:40 (mass) blend of acetone, Techspray's FLUX REMOVER AMS and xylene. The topcoat membrane can be formed having the total amount of solids between about 20 and 200 µg, for example, about 30 µg.

Example 8

A primer layer and a drug-polymer layer can be applied onto a stent as described in Example 1, the drug-polymer layer having the total amount of EVAL between about 300 and 800 µg, for example, about 380 µg. A topcoat composition to control the drug release rate can be prepared, comprising between about 0.1 mass % and about 15 mass %, for example, about 2.0 mass % of a 1:1 (by mass) blend of P(MMA-BMA) and PBMA, and the balance of a solvent system, for example, the solvent system including a 10:50:40 (mass) blend of acetone, Techspray's FLUX REMOVER AMS and xylene. The P(MMA-BMA)/PBMA blend can have about 83.3 mass % of units derived from BMA. The topcoat membrane can be formed having the total amount of solids between about 20 and 200 µg, for example, about 30 µg.

Example 9

A primer layer and a drug-polymer layer can be applied onto a stent as described in Example 1, the drug-polymer layer having the total amount of EVAL between about 300 and 800 µg, for example, about 350 µg. A topcoat composition to control the drug release rate can be prepared, comprising between about 0.1 mass % and about 15 mass %, for example, about 2.0 mass % of a 2:1 (by mass) blend of P(MMA-BMA) and PBMA, and the balance a solvent system, for example, a solvent system including a 10:50:40 (mass) blend of acetone, Techspray's FLUX REMOVER AMS and xylene. The P(MMA-BMA)/PBMA blend can have about 77.8 mass % of units derived from BMA. The topcoat membrane can have a total amount of solids between about 20 and 200 µg, for example, about 28 µg.

Example 10

A primer layer and a drug-polymer layer can be applied onto a stent as described in Example 9. A topcoat composition to control the drug release rate can be prepared, comprising between about 0.1 mass % and about 15 mass %, for example, about 2.0 mass % of a 4:1 (by mass) blend of P(MMA-BMA) and PBMA, and the balance a solvent system, for example, a solvent system including a 10:50:40 (mass) blend of acetone, Techspray's FLUX REMOVER AMS and xylene. The P(MMA-BMA)/PBMA blend can have about 73.3 mass % of units derived from BMA. The topcoat membrane can have a total amount of solids between about 20 and 200 µg, for example, about 32 µg.

Example 11

A primer layer and a drug-polymer layer can be applied onto a stent as described in Example 9. A topcoat composition to control the drug release rate can be prepared, comprising between about 0.1 mass % and about 15 mass %, for example, about 2.0 mass % of PEMA, and the balance a solvent system, for example, a solvent system including a 80:20 (mass) blend of acetone and cyclohexanone. Poly (ethyl methacrylate) having a weight-average molecular weight $M_w$ of about 101,400 available from Aldrich Chemical Company is one example of a brand of PEMA that can be used. In a manner identical to the application of the primer layer and the drug-polymer layer, the topcoat composition can be applied onto the dried drug-polymer layer. A number of spray passes can be performed followed by final baking, first at about 60° C. for about 2 hours and then at about 140° C. for about 1 hour. The topcoat membrane can be formed, the membrane having a solids content of between about 20 µg and about 300 µg, for example, about 40 µg.

Example 12

A primer layer and a drug-polymer layer can be applied onto a stent as described in Example 9. A topcoat composition to control the drug release rate can be prepared, comprising between about 0.1 mass % and about 15 mass %, for example, about 2.0 mass % of a blend of PEMA with a fluorinated polymer; and the balance a solvent system, for example, a solvent system including a 50:50 (mass) blend of acetone and cyclohexanone. The brand of PEMA described in Example 10 can be used. One example of the fluorinated polymer that can be used in a blend with PEMA is PVDF-HFP, such as SOLEF 21508 having about 85 mass % of vinylidene fluoride-derived units and about 15 mass % of hexafluoro propene-derived units. SOLEF 21508 is available from Solvay Fluoropolymers, Inc. of Houston, Tex. The PEMA/SOLEF 21508 blend can be 3:1 (mass) (containing about 75 mass % of PEMA and about 25 mass % of SOLEF 21508). In a manner identical to the application of the primer layer and the drug-polymer layer, the topcoat composition can be applied onto the dried drug-polymer layer. A number of spray passes can be performed followed by final baking, first at about 60° C. for about 2 hours and then at about 100° C. for about 1 hour. The topcoat membrane can have a solids content of between about 20 µg and about 300 µg, for example, about 42 µg.

Example 13

A stent was coated as described in Example 12, except instead of the 3:1 PEMA/SOLEF 21508 blend, a 3:1 (mass) blend of PEMA/PBMA can be used to form the topcoat membrane. The dry topcoat membrane can have a solids content of between about 20 µg and about 300 µg, for example, about 50 µg.

Example 14

A stent was coated as described in Example 13, except instead of the 3:1 PEMA/PBMA blend, a 1:1 (mass) blend of PEMA/PBMA can be used to form the topcoat membrane (containing about 50 mass % of PEMA and about 50 mass % of PBMA).

Example 15

A primer layer and a drug-polymer layer can be applied onto a stent as described in Example 4. A topcoat composition to control the drug release rate can be prepared, comprising between about 0.1 mass % and about 15 mass %, for example, about 2.0 mass % of a 1:1 (by mass) blend of PBMA and EVAL, and the balance a solvent system, for example, a solvent system including a 80:20 (mass) blend of DMAC and pentane. The topcoat membrane can have a total amount of solids of between about 20 and 200 µg, for example, about 30 µg.

Example 16

A primer layer can be applied onto a stent as described in Example 1. A drug formulation can be prepared comprising:

(a) between about 0.1 mass % and about 15 mass %, for example, about 2.0 mass % of a 1:1 (by mass) blend of PBMA and EVAL;

(b) between about 0.1 mass % and about 2 mass %, for example, about 1.6 mass % of a therapeutically active substance, for example, Everolimus; and (c) the balance, a solvent system, for example, a solvent system which includes a 80:20 (mass) blend of DMAC and pentane.

The drug containing formulation can then be applied onto the stent. The solids contents of the drug-polymer layer can be 1,200 μg.

Example 17

A primer layer and a drug-polymer layer can be applied onto a stent as described in Example 16. A topcoat composition to control the drug release rate can be prepared, comprising between about 0.1 mass % and about 15 mass %, for example, about 2.0 mass % PBMA and the balance a solvent system, for example, a solvent system including a 10:50:40 (mass) blend of acetone, Techspray's FLUX REMOVER AMS and xylene. The topcoat membrane can have a solids content of between about 20 μg and about 200 μg, for example, about 30 μg.

Example 18

A primer layer and a drug-polymer layer can be applied onto a stent as described in Example 16. A topcoat composition to control the drug release rate can be prepared as described in Example 15. The topcoat membrane can have a total amount of solids between about 20 and 200 μg, for example, about 30 μg.

Example 19

A primer layer and a drug-polymer layer can be applied onto a stent as described in Example 1. A topcoat composition to control the drug release rate can be prepared as described in Example 15. The topcoat membrane can be formed, in a manner identical to that described in Example 1, the topcoat membrane having the total amount of solids between about 20 and 200 μg, for example, about 30 μg.

Example 20

A primer layer and a drug-polymer layer can be applied onto a stent as described in Example 16. A topcoat composition to control the drug release rate can be prepared, the composition comprising between about 0.1 mass % and about 15 mass %, for example, about 2.0 mass % EVAL and the balance DMAC solvent The topcoat membrane can be formed, in a manner identical to that described in Example 1.

The information discussed in Examples 1-20 is summarized in Table 4.

TABLE 4

Summary of Examples 1–20

| Example No. | Polymer of the Drug-Polymer Layer | Drug | Polymer of the Topcoat Matrix |
|---|---|---|---|
| 1 | EVAL | Everolimus | PBMA |
| 2 | EVAL | Estradiol | PBMA |
| 3 | EVAL | Etoposite | PBMA |
| 4 | PBMA | Everolimus | PBMA |
| 5 | PBMA | Everolimus | None |
| 6 | P(MMA-BMA) | Everolimus | None |
| 7 | EVAL | Everolimus | P(MMA-BMA) |
| 8 | EVAL | Everolimus | 1:1 blend of P(MMA-BMA) and PBMA |
| 9 | EVAL | Everolimus | 2:1 blend of P(MMA-BMA) and PBMA |
| 10 | EVAL | Everolimus | 4:1 blend of P(MMA-BMA) and PBMA |
| 11 | EVAL | Everolimus | PEMA |
| 12 | EVAL | Everolimus | 3:1 blend of PEMA and P(VDF-HFP) |
| 13 | EVAL | Everolimus | 3:1 blend of PEMA and PBMA |
| 14 | EVAL | Everolimus | 1:1 blend of PEMA and PBMA |
| 15 | PBMA | Everolimus | 1:1 blend of PBMA and EVAL |
| 16 | 1:1 blend of PBMA and EVAL | Everolimus | None |
| 17 | 1:1 blend of PBMA and EVAL | Everolimus | PBMA |
| 18 | 1:1 blend of PBMA and EVAL | Everolimus | 1:1 blend of PBMA and EVAL |
| 19 | EVAL | Everolimus | 1:1 blend of PBMA and EVAL |
| 20 | 1:1 blend of PBMA and EVAL | Everolimus | EVAL |

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A coating for an implantable medical device, comprising a layer comprising:
a copolymer comprising butyl methacrylate and one or two other alkyl acrylates or alkyl methacrylates; or,
the aforementioned copolymer blended with one or more other non-acrylate polymers or copolymers; and,
a therapeutically active agent, wherein:
the alkyl of the one or two other acrylates or methacrylates is a $C_1$ to $C_{12}$ straight chained or branched aliphatic radical; and,
the layer is free of acetate species.

2. The coating of claim 1, wherein the implantable medical device is a stent.

3. The coating of claim 1, wherein the therapeutically active agent is rapamycin a derivative thereof or an analog thereof.

4. The coating of claim 1, wherein the butyl methacrylate copolymer comprises an n-butyl methacrylate copolymer.

5. The coating of claim 1, wherein the non-acrylate polymers or copolymers are fluorinated polymers or copolymers.

6. The coating of claim 5, wherein the fluorinated polymer or copolymer is selected from the group consisting of poly(vinylidene fluoride) and poly(vinylidene fluoride-co-hexafluoropropene).

7. A coating for an implantable medical device, the coating comprising a first layer having an active agent incorporated therein and a second layer disposed over the first layer, wherein the second layer comprises:
a copolymer comprising butyl methacrylate and one or two other alkyl acrylates or alkyl methacrylates; or,
the aforementioned copolymer blended with one or more other non-acrylate polymers or copolymers; wherein:
the alkyl of the one or two other acrylates or methacrylates is a $C_1$ to $C_{12}$ straight chained or branched aliphatic radical; and,
the second layer is free from acetate species.

8. The coating of claim 7, wherein the implantable medical device is a stent.

9. The coating of claim 7, wherein the agent is for reducing, inhibiting or lowering the incidence of restenosis.

10. The coating of claim 7, wherein the butyl methacrylate copolymer comprises poly(n-butyl methacrylate).

11. The coating of claim 7, wherein the non-acrylate polymers or copolymers are fluorinated polymers or copolymers.

12. The coating of claim 11, wherein the fluorinated polymer or copolymer is selected from the group consisting of poly(vinylidene fluoride) and poly(vinylidene fluoride-co-hexafluoropropene).

13. A method of coating an implantable medical device, comprising depositing a first layer on the device, the first layer including an active agent for the sustained release of the agent, and depositing a second layer over the first layer, the second layer comprising:
a copolymer comprising butyl methacrylate and one or two other alkyl acrylates or alkyl methacrylates; or,
the aforementioned copolymer blended with one or more other non-acrylate polymers or copolymers; wherein:
the alkyl of the one or two other acrylates or methacrylates is a $C_1$ to $C_{12}$ straight chained or branched aliphatic radical; and,
the second layer is free of acetate species.

14. The method of claim 13, wherein the implantable medical device is a stent.

15. The method of claim 13, wherein the therapeutically active agent is rapamycin, a derivative thereof or an analog thereof.

16. The method of claim 13, wherein the butyl methacrylate copolymer comprises an n-butyl methacrylate copolymer.

17. The coating of claim 1, wherein the non-acrylate polymer is poly(ethylene-co-vinyl alcohol).

18. The coating of claim 7, wherein the non-acrylate polymer is poly(ethylene-co-vinyl alcohol).

19. The coating of claim 13, wherein the non-acrylate polymer is poly(ethylene-co-vinyl alcohol).

20. The coating of claim 1, wherein the therapeutically active agent is a 40-O-derivative of rapamycin.

21. The method of claim 13, wherein the therapeutically active agent is a 40-O-derivative of rapamycin.

* * * * *